(12) United States Patent
Ohlrogge et al.

(10) Patent No.: US 6,192,737 B1
(45) Date of Patent: Feb. 27, 2001

(54) METHOD FOR MEASURING THE CONCENTRATION OF A DISSOLVED GAS IN A FLUID

(75) Inventors: Klaus Ohlrogge, Geesthacht; Carsten Hasler, Hamburg; Jan Wind, Lauenburg; Dieter Cegla, Seevetal; Franz Josef Steffens, Bayrischzell, all of (DE)

(73) Assignees: Rosemount Analytical Inc., Irvine, CA (US); GKSS-Forschungszentrum Geesthacht GmbH, Geesthacht (DE)

( * ) Notice: Subject to any disclaimer, the term of this patent is extended or adjusted under 35 U.S.C. 154(b) by 0 days.

(21) Appl. No.: 09/197,128

(22) Filed: Nov. 20, 1998

(30) Foreign Application Priority Data

Nov. 25, 1997 (DE) .............................. 197 51 971

(51) Int. Cl.[7] .............................. G01N 7/10; G01N 33/14
(52) U.S. Cl. ...................... 73/19.06; 73/19.01; 73/19.04; 73/19.05; 73/19.1; 261/104
(58) Field of Search .............................. 73/19.01, 19.04, 73/19.05, 19.06, 19.1; 261/104

(56) References Cited

U.S. PATENT DOCUMENTS

| | | | |
|---|---|---|---|
| 4,461,165 | * | 7/1984 | Kesson ................................. 73/19.05 |
| 4,517,135 | * | 5/1985 | Szerenyi et al. .................. 73/19.1 X |
| 4,550,590 | * | 11/1985 | Kesson ............................... 73/19.1 X |
| 5,144,831 | * | 9/1992 | Hale et al. ....................... 73/19.06 X |
| 5,255,553 | * | 10/1993 | Hale et al. ............................. 73/19.1 |

FOREIGN PATENT DOCUMENTS

| | | | |
|---|---|---|---|
| 44 39 715 | | 5/1996 | (DE) .................................... 73/19.06 |
| 0 429 397 | | 5/1991 | (EP) .................................... 73/19.05 |
| 1452574 | * | 3/1982 | (GB) .................................... 73/19.06 |
| 913152 | * | 3/1982 | (SU) ..................................... 73/19.1 |

* cited by examiner

Primary Examiner—Daniel S. Larkin
(74) Attorney, Agent, or Firm—Westman, Champlin & Kelly, P.A.

(57) ABSTRACT

The invention pertains to a method for measuring the concentration of dissolved gases in a liquid [(39)], especially of $CO_2$ in beverages, in which the liquid [(39)] is passed across the retentate side [(140)] of a membrane [(14)] that is at least partially permeable to the dissolved gas, and [in which] the volumetric flow of the permeated gas on permeate side [(16)] of the membrane [(14)] is determined, the temperature of the liquid [(39)] is measured, and the concentration of the dissolved gas in the liquid [(39)] is calculated from these values. In this, the thickness of the membrane [(14)] can be pre-selected as a function of the flow rate of the liquid [(39)] flowing along the retentate side [(140)].

8 Claims, 2 Drawing Sheets

METHOD FOR MEASURING THE CONCENTRATION OF A DISSOLVED GAS IN A FLUID

DESCRIPTION

The invention pertains to a method for measuring the concentration of dissolved gases in a liquid, especially of $CO_2$ in beverages, in which the liquid is passed across the retentate side of a membrane that is at least partially permeable to the dissolved gas, and [wherein] the volumetric flow of the permeated gas on permeate side of the membrane is determined, the temperature of the liquid is measured, and the concentration of the dissolved gas in the liquid is calculated from these values.

A method of this kind is known (DE-OS [Offenlegungsschrift=disclosure] 44 39 715) deriving from the same applicants. This known method has proven to be extraordinarily effective and economical as well as being easily used in practice, especially in connection with concentration measurement of dissolved carbon dioxide ($CO_2$) in water or beverages.

For certain applications, especially in the area of analysis, a still higher accuracy is frequently needed in determination of the dissolved gas concentration in a liquid.

It is generally known that some beverages that are bottled in cans or bottles, for example, cola, soft drinks, or mineral water, frequently contain carbon dioxide in dissolved form. In manufacture, one proceeds so that prior to filling into bottles, cans, or the like, a specific amount of gaseous carbon dioxide is added to the beverage so that a part of the carbon dioxide is taken up by the beverage. In this, attention must be paid that the content of carbon dioxide is maintained within certain limits. On the one hand, the beverage should still contain an adequate amount of carbon dioxide upon consumption, and on the other, the beverage must not foam upon opening of the container, which can be traced to too high an amount of carbon dioxide.

During the filling operation, the concentration must be monitored and possibly adjusted. Methods and apparatuses for measuring the carbon dioxide content or carbon dioxide concentration are known with which the carbon dioxide concentration can be determined discontinuously. For this purpose, samples are generally taken from the ongoing production process and these are studied with regard to the carbon dioxide concentration. The dosing of carbon dioxide is influenced based on the results. This discontinuous method of measurement has the disadvantage that, for example, short-term variations cannot be detected or lead to erroneous analyses so that even with more frequent measurements, rejects cannot be avoided. Especially with too-high a carbon dioxide concentration in the liquid, there is the danger that the container for the end user will burst, for example, at higher temperatures and/or more vigorous movement wherein the danger of injuring the user cannot be excluded.

The known method is based on the recognition that with given membrane characteristics, namely the gas permeability and the membrane area, the volumetric flow of gas through the membrane can be used as a measure of the concentration of the gas in the liquid on the retentate side of the membrane. The volumetric flow of the permeate, i.e., the volumetric flow of the dissolved gas, depends on the permeability, the membrane area, and the driving pressure difference across the membrane as well as the concentration of the gas dissolved in the liquid on the retentate side of the membrane. The concentration of gas dissolved in the liquid on the retentate side that is required for creating the measured volumetric flow of the gas on the permeate side depends on the pressure on the retentate side in a manner that depends on the temperature of the liquid and which is unique for the respective substance mixture, namely via the Henry's Law coefficient. Specifically, this means that the measured volumetric flow at a particular temperature is a measure of the concentration of the dissolved gas on the retentate side of the membrane.

It is irrelevant for the functioning of the membrane whether the liquid with the dissolved gas is supersaturated, saturated, or less than saturated. Also, the actual pressure on the retentate side does not necessarily need to be determined. Rather, in the method of the invention, use is made of the fact that a certain concentration of substance on the retentate side of the membrane at a given temperature causes a certain volumetric flow of the dissolved gas through the membrane.

With the known method, it is possible to perform continuous measurement of the dissolved gas in a liquid. In mixing beverages with carbon dioxide, it is therefore possible, for example, that a computing unit used for evaluation of the measured values (temperature, volumetric flow) be connected to a control unit by which the dosing device for carbon dioxide is controlled. In this manner it is possible to make available an essentially closed regulatory circuit for dosing of carbon dioxide in the preparation of beverages.

It is the goal of the invention to create a method with which such a highly accurate continuous measurement of the concentration of a gas dissolved in a liquid is possible so that it can be used in the field of analysis, wherein the method itself should be able to be done by simple means and thus inexpensively, and that apparatus for doing the process is used that is essentially commercially available and thus likewise contributes to the inexpensive execution of the process.

This goal is attained by the invention in that the thickness of the membrane can be preselected as a function of the velocity of the liquid flowing past the retentate side.

This procedure has the advantage that, besides the values to be measured, namely the volumetric flow on the one hand and the temperature on the other which can be continuously determined, there is also an adjustment of the membrane thickness, and therefore of the permeation rate of the dissolved gases through the membrane as a function of the boundary layer formation at the membrane surface, to the velocity of the liquid and it is included in the calculation, so that for example, by using the computing unit, the concentration of the gas content [sic] in the liquid can be indicated continuously with sufficient accuracy so that the method is also suitable for application in the field of analysis as is strived for.

According to an advantageous embodiment of the method, the flow rate of the liquid is determined, wherein a calculation of the dissolved gas in the liquid is interrupted, as a pre-set minimum flow rate in the liquid is detected. Below a minimum [flow] rate of a liquid, a boundary layer in the liquid can no longer be formed at the retentate side of the membrane, i.e., at the surface there, to the extent desired so that measurements below a minimum flow rate falsify the calculated measurement results and possibly make them completely unusable.

In a further advantageous embodiment of the method, the level of the minimum flow rate can be set, i.e., the threshold at which the measured parameters are determined or a calculation is or is not done, so that an immediate adjustment to the measurement goal as such, to the liquid and the solubility of the gas in the liquid, is thereby possible.

In order to further increase the accuracy of the concentration determination, it is advantageous to use the flow rate of the liquid as such for calculation of the concentration of the dissolved gas in the liquid in addition to the determined volumetric flow of the permeating gas and the temperature of the liquid so that, as already described above, the effect of the flow rate of the liquid on boundary layer formation on the retentate side of the membrane can come into the calculation.

A further improvement in the accuracy of the concentration determination is advantageously attained in that besides the determined volumetric flow of the permeating gas and the temperature of the liquid, the ambient pressure is also used for calculating the concentration of the dissolved gas in the liquid, wherein due to the additional determination of the ambient air pressure, a correction of the value for permeation of the gas through the membrane is possible since the ambient air pressure acts as atmospheric counter-pressure to the permeation.

In a still further advantageous embodiment of the method for determining the concentration of a dissolved gas in a liquid, the solubility coefficient of the gas or of different gases, which is different in different liquids, is used and likewise is included as a determining parameter in the overall calculation, whereby a still more accurate concentration determination is possible.

Depending on apparatus-related conditions that have an effect on the procedure of doing the method, strong changes in the determined parameters like [sic; as well as] the gas concentration that is calculated from them have an effect on the rapidity of the measurement of the parameters and the concentration level calculated from them. The larger the changes in the measured values from one measuring time to another and thus from one time of calculation to another, the larger will be the average time for evaluation, that is, the time required for and between calculation processes, so that it is extraordinarily advantageous to determine the final measured value by calculation or estimation from the slope of a parameter in order to shorten the equilibration time when there are changes in the measured values and in this manner obtain an intelligent set-up for attaining an overall rapid determination of the concentration of the gas in the liquid with quasicontinuous measurements even with large changes in the measured values.

With wear, down time, or other effects impairing the functioning of the apparatus for performing the method of the invention, after appropriate repair or exchange of parts, especially also of the membrane, a new calibration of the apparatus for doing the method is required. Calibration of a computing or evaluating unit used in performing the method is advantageously done by using a pure gas whose parameters are known, wherein this pure gas is preferably $CO_2$.

The invention is described in more detail on the basis of the following schematic drawing[s] wherein.

Figure 1:
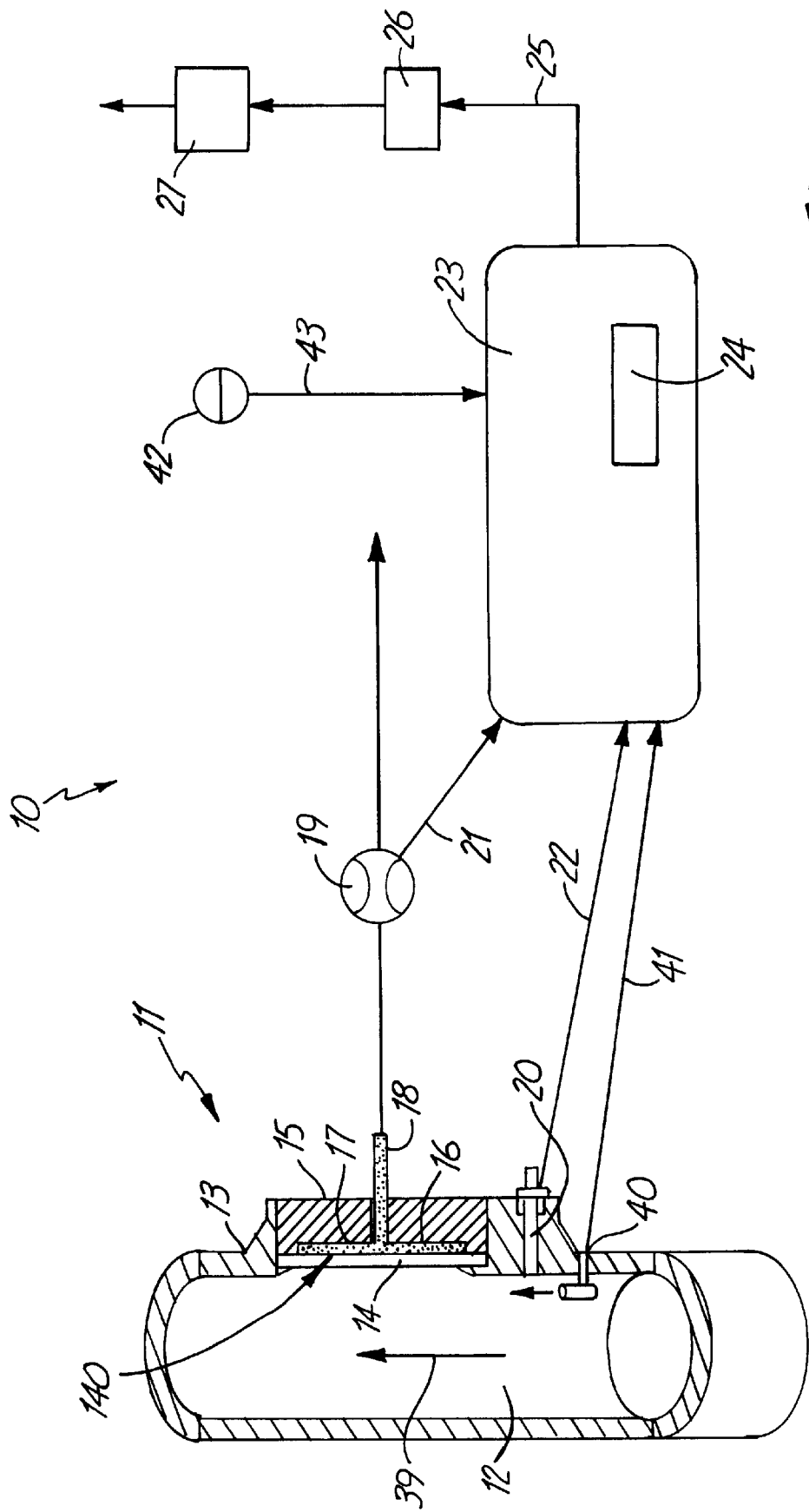
FIG. 1 is a schematic diagram of a device of the invention.
Figure 2:
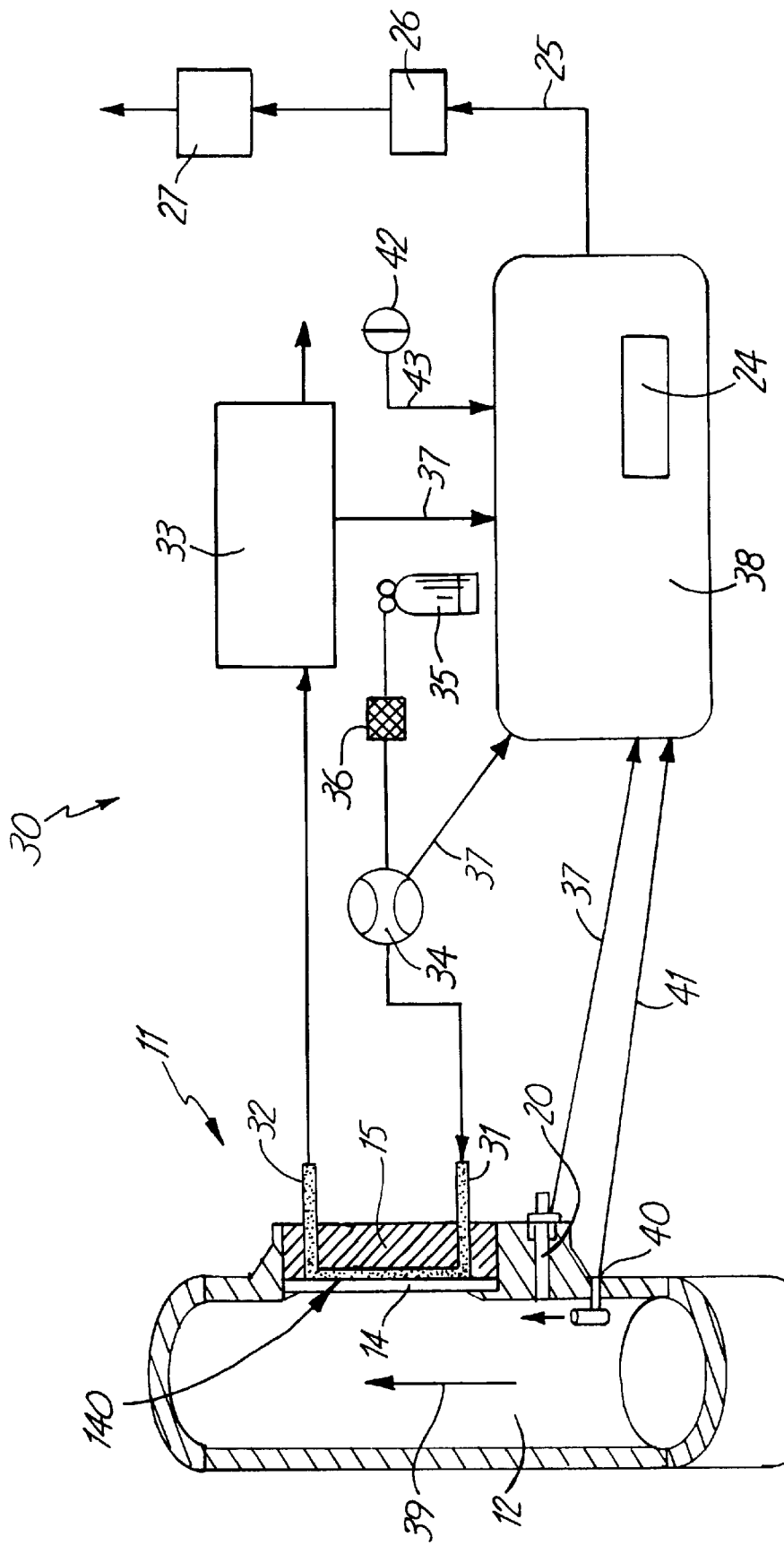
FIG. 2 is a schematic diagram of a device of the invention in another embodiment.

With respect to their basic construction, the devices 10 and 30 in FIGS. 1 and 2 essentially correspond to the devices 10 as they are known from the known, related DE-OS 44 39 715. The device 10 for measuring the concentration of a gas in a liquid has a measuring vessel 11 that is formed as a measuring sensor which is equipped with an essentially tubular measuring channel 12. There is a membrane 14 in the wall 13 surrounding the measuring channel 12, [which membrane] is connected to the measuring vessel 11 via an appropriate membrane holding device 15. In this, the surface of the membrane 14 is oriented so that its retentate side 140 is essentially parallel to the direction of flow of the liquid 39 in the measuring channel 12.

The permeate side 16 of membrane 14 that is away from the liquid 39 is connected to a cavity 17 whose outlet 18 is connected to a flowmeter 19. Heretofore, it was possible with this arrangement to measure the volumetric flow of a gas passing through the membrane, for example carbon dioxide.

Additionally, in wall 13 of the measuring channel 12 in the region of the membrane 14, there is a measuring device 20 for determining the temperature of the liquid 39. Moreover, in measuring channel 12, there is a flow rate indicator 40 for determining the flow rate of the liquid 39.

The signal output of the flowmeter 19 is connected to a computing unit 23 via a signal line 21, as is the signal output of the temperature measuring device 20 via signal line 22. The signal output of the flow rate indicator 40 is likewise connected with the computing unit 23 via a signal line 41. The concentration of dissolved gas in the liquid is calculated in this computing unit 23 based on the determined values, namely the volumetric flow of the permeated gas stream on one side and the temperature of the liquid 39 on the other side, the [flow] rate of the liquid 39, and the ambient air pressure.

Finally, there is an air pressure gauge 42 that likewise via a signal line 43 supplies the appropriate air pressure values at predetermined time intervals quasicontinuously to the computing unit 23.

For example, the concentration of dissolved $CO_2$ in water in this measuring device is obtained from:

$$c_{CO_2} = \left[\frac{\dot{V}}{L \cdot A} + P_P\right] \cdot N \cdot H(T)$$

wherein
V is the volumetric flow in $m^3/h$
L is the permeability of $CO_2$, $m^3 N/m^2 \cdot h \cdot bar$
A is the membrane area, $m^2$
$P_p$ is the permeate pressure, bar
T is the temperature, °C
$N$ is the density of $CO_2$ under normal conditions, (1.97 $kg/M^3$)
$C_{CO2}$ is the carbon dioxide concentration, g $CO_2$ per 1 of water
H is the Henry's Law coefficient, $m^3{}_{CO2}/m^3{}_w \cdot bar$
In this relation, the H(T) function (Henry's Law coefficient) depends on the temperature and, for a $CO_2$-water mixture, is: [In equations, commas in numbers represent decimal points.]

$$H = 1,6431 - 0,059017 \cdot T + 0,0012226 \cdot T^2 - 1,36E - 05T^3 + 6,17E - 08T^4$$

$$0° < T < 60°$$

The computing unit 23 is equipped with an indicator 24 by means of which the $CO_2$ concentration determined in the liquid can be indicated. It can also be arranged that the signal output of the computing unit 23 is connected via a signal line 25 to a controlling unit 26. The controlling unit 26 can be connected, for example, to a dosing device for $CO_2$ 27 of a beverage bottling plant that is not shown. In this manner, in bottling of beverages, it is possible to control dosing of the $CO_2$ directly via the measured $CO_2$ concentration.

The device 30 for measuring the concentration of dissolved gases in a liquid shown in FIG. 2 essentially corresponds to the device 10 in FIG. 1 so that the same elements are designated with the same reference numbers. In device 30 of FIG. 2, the measuring vessel 11 is essentially identical with the measuring vessel of device 10 in FIG. 1. Here however, a rinsing gas can flow across the free space 17 on the permeate side 16 of membrane 14. Specifically, the device is constructed in such a manner that the membrane holding device 15 which adjoins the free space 17 on the permeate side 16 of the membrane 14 is equipped with an inlet 31 for rinsing gas and an outlet 32 for the rinsing gas/gas mixture. In the embodiment shown in FIG. 2, rinsing gas is passed co-current to the liquid in measuring channel 12. It is of course also possible that the rinsing gas be passed counter-current or cross-current to the liquid. As rinsing gas, nitrogen can preferably be used.

The outlet 32 for the nitrogen-gas mixture is connected with a measuring device 33 for determining the concentration of gas in the rinsing gas stream. The inlet 31 is connected with a flowmeter 34 to determine the volumetric flow of the rinsing gas. At the other end of the inlet 31, there is a rinsing gas supply 35 as well as a filter 36 for the rinsing gas.

The signal outputs of the temperature measuring device 20, the flowmeter 34, and the concentration measuring device 33 are connected via signal lines 37 to a computing unit 38 as are the air pressure gauge 42 via signal line 43 and the flow rate indicator meter 40 for measuring the flow rate of the liquid 39 via signal line 41, which [computing unit] calculates the concentration of the dissolved gas in the liquid 39 from the determined values.

In this embodiment, the concentration of dissolved $CO_2$ in water can be determined, for example, as follows:

$$c_{CO_2} = \left[\frac{\dot{V}}{L \cdot A}\right] \cdot N \cdot H(T)$$

The H(T) function corresponds to the above-indicated function. In this, the permeate pressure $P_p$ is negligible since the amount of rinsing gas is advantageously adjusted in such a manner that the partial pressure of the carbon dioxide in the rinsing gas stream is relatively low.

In the embodiment shown in FIG. 2, the flow measuring device 34 is situated in the inlet line 31 for the rinsing gas. It is of course also possible that the flow measuring device 34 be situated behind the outlet 32 in front of or behind the concentration measuring device 33.

The computing unit 38 has an indicator 24 for the concentration of the dissolved gas in the liquid. Of course, here too, the signal output can be connected in an appropriate manner via a signal line 25 to a control unit 26 that controls a dosing device 27, for example for addition of $CO_2$ in a beverage bottling plant.

List of reference numbers
10 Device
11 Measuring vessel
12 Measuring channel
13 Wall
14 Membrane
140 Retentate side
15 Membrane holding device
16 Permeate side
17 Free space
18 Outlet
19 Flowmeter
20 Temperature measuring device
21 Signal line
22 Signal line
23 Calculating unit
24 Indicator
25 Signal line
26 Control unit
27 Dosing device
30 Device
31 Inlet
32 Outlet
33 Concentration measuring device
34 Flowmeter
35 Rinsing gas supply
36 Filter
37 Signal line
38 Calculating unit
39 Liquid
40 Flow rate indicator
41 Signal line
42 Air pressure gauge
43 Signal line

What is claimed is:

1. Method for measuring the concentration of dissolved gases in a liquid, especially of $CO_2$ in beverages, in which the liquid is passed across the retentate side of a membrane that is at least partially permeable to the dissolved gas, and the volumetric flow of the permeated gas on the permeate side of the membrane is determined, the temperature of the liquid is measured, and the concentration of the dissolved gas in the liquid is calculated from these values, characterized by the fact that the thickness of the membrane can be preselected as a function of the flow rate of the liquid flowing along the retentate side.

2. Method as per claim 1, characterized by the fact that the flow rate of the liquid is determined, wherein the calculation of the concentration of dissolved gas in the liquid is interrupted as a pre-set minimum flow rate of the liquid is detected.

3. Method as per claim 1, characterized by the fact that a level of a minimum flow rate can be adjusted.

4. Method as per claim 1, characterized by the fact that besides the determined volumetric flow of the permeating gas and the temperature of the liquid the ambient air pressure is also used for calculating the concentration of the dissolved gas in the liquid.

5. Method as per claim 1, characterized by the fact that to determine the concentration of the dissolved gas in the liquid, the various solubility coefficients of the gas in different liquids is used.

6. Method as per of claim 1, characterized by the fact that a final measured value is calculated or estimated from the slope of a parameter.

7. Method as per claim 1, characterized by the fact that in performing the method, calibration of the computing or evaluating unit is done using a pure gas whose parameters are known.

8. Method as per claim 7, characterized by the fact that the pure gas is $CO_2$.

* * * * *